United States Patent [19]

Hefner et al.

[11] Patent Number: 5,312,938
[45] Date of Patent: May 17, 1994

[54] HOMOGENEOUS CATALYSTS AND OLEFIN POLYMERIZATION PROCESS

[75] Inventors: John G. Hefner; Brian W. S. Kolthammer, both of Lake Jackson, Tex.

[73] Assignee: The Dow Chemical Company, Midland, Mich.

[21] Appl. No.: 42,027

[22] Filed: Apr. 2, 1993

Related U.S. Application Data

[60] Division of Ser. No. 897,719, Jun. 12, 1992, abandoned, which is a continuation-in-part of Ser. No. 586,629, Sep. 20, 1990, abandoned.

[51] Int. Cl.$^5$ .................... C07F 7/28; C07F 17/00
[52] U.S. Cl. ........................ 556/11; 556/12; 556/52; 556/56
[58] Field of Search .............. 556/11, 12, 52, 56

[56] References Cited

U.S. PATENT DOCUMENTS

| | | | |
|---|---|---|---|
| 4,120,820 | 10/1978 | Birkelbach | 252/429 B |
| 4,189,553 | 2/1980 | Birkelbach | 526/92 |
| 4,713,401 | 12/1987 | Riediker et al. | 522/65 |
| 4,719,193 | 1/1988 | Levine et al. | 502/107 |
| 4,855,468 | 8/1989 | Riediker et al. | 556/53 |
| 5,045,517 | 3/1991 | Campbell et al. | 502/103 |

FOREIGN PATENT DOCUMENTS 0271874  6/1988  European Pat. Off.

OTHER PUBLICATIONS

Burger et al., J. Organomet. Chem., vol. 101, pp. 295-306 (1975).
Chemical Abstracts, vol. 75, No. 2, 12 Jul. 1971, Abstract No. 7386n, Columbus, Ohio, U.S.; P. T. Joseph, et al.: "Diindenyl-and bis(2-aminofluorenyl)titanium dichlorides".
"Polymerization of Olefins with Homogeneous Zirconocene/Aluminoxane Catalysts" by W. Kaminsky and R. Steiger, Polyhedron, vol. 7, No. 22/23, pp. 2375-2381, 1988.
Chem. Abst. 84:30228g (1976).
Chem. Abst. 84:31206k (1976).
Chem. Abst. 94:47815a (1981).
Chem. Abst. 95:187370x (1981).

Primary Examiner—José G. Dees
Assistant Examiner—Porfirio Nazario-Gonzalez

[57] ABSTRACT

Olefins are polymerized in the presence of a homogeneous catalyst represented by the formula $LTi(NR_2)_3$ wherein L is a $\pi$-bonded ligand selected from the group consisting of indenyl, $C_1$-$C_4$ alkyl substituted indenyl, —$OSiR_3$ substituted indenyl, R is a $C_1$-$C_4$ alkyl group wherein each R attached to the same nitrogen atom is the same, but the R groups attached to different nitrogen atoms can be the same or different from those attached to the other nitrogen atoms.

5 Claims, No Drawings

HOMOGENEOUS CATALYSTS AND OLEFIN POLYMERIZATION PROCESS

CROSS-REFERENCE TO RELATED APPLICATION

This application is a division of application Ser. No. 07/897,719 file Jun. 12, 1992, now abandoned which is a continuation-in-part of application Ser. No. 07/586,629 filed Sep. 20, 1990, now abandoned, which is incorporated herein by reference in its entirety.

FIELD OF THE INVENTION

The present invention pertains to homogeneous catalyst complexes which can be activated with or without the presence of a cocatalyst or activator compound and to a process for polymerizing α-olefins in the presence of these catalysts.

BACKGROUND OF THE INVENTION

Several examples of homogeneous olefin polymerization catalysts appear in the literature for a variety of transition (W. Kaminsky & R. Steiger in *Polyhedron*, 1988, vol. 7, no. 22/23, pp. 2375–2381), lanthanide (P. L. Watson in *J. Am. Chem. Soc.*, 1982, vol. 104, no. 1, pp. 337–339) and actinide (P. J. Toscano and T. J. Marks in *J. Am. Chem. Soc.*, 1985, vol. 107, no. 3, pp 653–659) metal complexes. Most of the homogeneous olefin polymerization catalysts reported to date require the use of a soluble cocatalyst such as methylaluminoxanes (MAO). One particular advantage of the homogeneous catalysts is the absence of corrosive components in the formulation and reduction of the number of components required to prepare them, as compared to a typical heterogeneous catalyst. Several disadvantages limit the utility of this method of catalysis in industrial olefin polymerization processes. These include the expense of MAO due to the extremely high ratios of MAO frequently needed to efficiently polymerize olefins, batch to batch variation of the MAO and generally low molecular weight products are obtained which have limited application.

R. F. Jordan in *J. Chem. Ed.*, 1988, vol. 65, no. 4, pp 285–289 discloses another form of homogeneous olefin polymerization which includes cationic polymerization catalysts. These polymerization catalysts generally produce polymers with narrow molecular weight distributions and high molecular weights. They generally contain a transition metal component such as titanium or zirconium with a cyclopentadienyl group or other cyclodienyl group and a cation prepared from the reaction with a salt. The complexes are generally very air sensitive and require special handling. The polymerization reaction is very solvent dependent and generally requires solvents, such as methylene chloride, diethyl ether and tetrahydrofuran, not typically used in the industrial preparation of ethylene polymers.

Complexes of the general type $LTiX_3$ have been disclosed by R. E. Campbell and J. G. Hefner in U.S. Patent Application Ser. No. 07/462,861, filed Jan. 5, 1990 for the preparation of syndiotactic polystyrene where L is a n-bonded group such as cyclopentadienyl or indenyl and X is an alcohol, halide or amide. A cocatalyst is required for the polymerization reaction such as MAO (methylaluminoxane) in a range of Al:Ti atomic ratio of from about 50:1 to about 10,000:1. For any polymerization reaction it is highly desirable to eliminate or reduce the amount of MAO required as it is expensive and difficult to produce with consistency.

D. F. Birkelbach in U.S. Pat. No. 4,120,820 and U.S. Pat. No. 4,189,553 has also disclosed a more complex mixture for the polymerization of olefins utilizing Ti complexes of the general formula $LTiX_3$ in which X is a halide and L is an electron donor. The nature of the L group does not describe specifically a n-donor as used in this art. Furthermore, this mixture required components such as a dialkyl magnesium and an alkylaluminum or an alkylaluminum halide in order to produce an active catalyst.

It would be desirable to have available a catalyst with a reduced number of components required to produce an active catalyst for the polymerization of α-olefins.

SUMMARY OF THE INVENTION

One aspect of the present invention pertains to a catalytic compound represented by the formulas $LTi(NR^1{}_2)_3$ or $LTi(NR^1{}_2)_2X$ wherein L is a n-bonded ligand selected from the group consisting of indenyl, $C_1$–$C_4$ alkyl substituted indenyl, —$OSiR_3$ substituted indenyl; each $R^1$ group attached to the same nitrogen atom is the same, however, the $R^1$ groups attached to different nitrogen atoms can be the same or different from those attached to other nitrogen atoms and are $C_1$–$C_4$ alkyl groups; and X is a halogen, preferably chlorine or bromine.

Another aspect of the present invention pertains to a process for preparing catalytic compounds represented by the formula $LTi(NR^1{}_2)_3$ wherein L is a $_{II}$-bonded ligand selected from the group consisting of indenyl, $C_1$–$C_4$ alkyl substituted indenyl, —$OSiR_3$ substituted indenyl, and each $R^1$ is the same and is a $C_1$–$C_4$ alkyl group which process comprises (1) reacting a compound represented by the formula $Ti(NR^1{}_2)_4$ wherein each R is the same and is a $C_1$ to $C_4$ alkyl group; with a compound represented by the formula R′(Ind) wherein R′ is hydrogen, a $C_1$ to $C_4$ alkyl group, —$OSiR_3$, —OR or a halogen, preferably chlorine, bromine or iodine; R is a $C_1$–$C_4$ alkyl group; and Ind is an indenyl group; and (2) recovering the desired product form the reaction mixture.

Another aspect of the present invention pertains to a process for preparing catalytic compounds represented by the formula $LTi(NR^1{}_2)_3$ wherein L is a $_{II}$-bonded ligand selected from the group consisting of indenyl, $C_1$–$C_4$ alkyl substituted indenyl, —$OSiR_3$ substituted indenyl; R is a $C_1$–$C_4$ alkyl group; and each $R^1$ is the same and is a $C_1$–$C_4$ alkyl group; which process comprises (1) reacting a compound represented by the formula $XTi(NR^1{}_2)_3$ wherein each $R^1$ is the same and is a $C_1$ to $C_4$ alkyl group; with a compound represented by the formula R′M(Ind) wherein M is an alkali metal; R′ is hydrogen, a $C_1$ to $C_4$ alkyl group, —$OSiR_3$, —OR or a halogen, preferably chlorine, bromine or iodine; X is a halogen atom, preferably chlorine, bromine or iodine; and Ind is an indenyl group; and (2) recovering the desired product form the reaction mixture.

Another aspect of the present invention pertains to a process for preparing compounds represented by the formula $LTi(NR^1{}_2)X_2$ wherein L is a $_{II}$-bonded ligand selected from the group consisting of indenyl, $C_1$–$C_4$ alkyl substituted indenyl, —$OSiR_3$ substituted indenyl; each $R^1$ is the same and is a $C_1$–$C_4$ alkyl group; and X is a halogen, preferably chlorine, bromine or iodine; which process comprises (1) reacting a compound represented by the formula $Ti(NR^1{}_2)X_3$; wherein $R^1$ is a $C_1$–$C_4$ alkyl group; with a compound represented by the formula R'M(Ind) wherein R' is a hydrogen, a $C_1$–$C_4$ alkyl group, —$OSiR_3$, —OR or a halogen, preferably chlorine, bromine or iodine; R is a $C_1$–$C_4$ alkyl group; Ind is an indenyl group; and M is an alkali metal; and (2) recovering the desired product from the reaction mixture.

Another aspect of the present invention pertains to a process for preparing compounds represented by the formula $LTi(NR^1_2)(NR^2_2)X$ wherein L is a $_{II}$-bonded ligand selected from the group consisting of indenyl, $C_1$–$C_4$ alkyl substituted indenyl, —$OSiR_3$ substituted indenyl; $R^1$ and $R^2$ are different and each $R^1$ and $R^2$ is independently a $C_1$–$C_4$ alkyl group; and X is a halogen, preferably chlorine, bromine or iodine; which process comprises (1) reacting any two compounds selected from the group consisting of (a) a compound represented by the formula $Ti(NR^1_2)X_3$, (b) $M(NR^2_2)$, and (c) R' (Ind)M wherein R' is hydrogen, a $C_1$–$C_4$ alkyl group, —$OSiR_3$, —OR or a halogen, preferably chlorine, bromine, or iodine, Ind is an indenyl group, M is an alkali metal, and R is a $C_1$–$C_4$ alkyl group; (2) separating the reaction product from the reactants; (3) reacting the product from step (2) with the component (b) or (c) not reacted in step (1); and (4) recovering the desired product.

Another aspect of the present invention pertains to a process for preparing catalytic compounds represented by the formula $LTi(NR^1_2)_2(NR^2_2)$ wherein L is a $_{II}$-bonded ligand selected from the group consisting of indenyl, $C_1$–$C_4$ alkyl substituted indenyl, —$OSiR_3$ substituted indenyl; $R^1$ and $R^2$ are different and each $R^1$ and $R^2$ is independently a $C_1$–$C_4$ alkyl group; and X is a halogen, preferably chlorine, bromine or iodine; which process comprises (1) reacting any two compounds selected from the group consisting of (a) a compound represented by the formula $TiX_2(NR^1_2)_2$, (b) $M(NR^2_2)$, and (c) R'(Ind)M wherein R' is hydrogen, a $C_1$–$C_4$ alkyl group, —$OSiR_3$, —OR or a halogen, preferably chlorine, bromine, or iodine, Ind is an indenyl group, M is an alkali metal, and R is a $C_1$–$C_4$ alkyl group; (2) separating the reaction product from the reactants; (3) reacting the product from step (2) with the component (b) or (c) not reacted in step (1); and (4) recovering the desired product.

Another aspect of the present invention pertains to a process for preparing catalytic compounds represented by the formula $LTi(NR^1_2)(NR^2_2)(NR^3_2)$ wherein L is a $_{II}$-bonded ligand selected from the group consisting of indenyl, $C_1$–$C_4$ alkyl substituted indenyl, —$OSiR_3$ substituted indenyl; and $R^1$, $R^2$ and $R^3$ are different and are independently a $C_1$–$C_4$ alkyl group; which process comprises (1) reacting a compound represented by any one of the formula $LTi(NR^1_2)(NR^2_2)X$ wherein $R^1$ and $R^2$, are different and are each independently a $C_1$–$C_4$ alkyl group; X is a halogen, preferably chlorine, bromine or iodine; and L is as defined above; with a compound represented by the formula $M(NR^3_2)$ wherein $R^3$ is a $C_1$–$C_4$ alkyl group different from $R^1$ and $R^2$, and M is Li, Na or K; and (2) recovering the desired product.

Another aspect of the present invention pertains to a process for polymerizing one or more monomers comprising one or more α-olefins or one or more α-olefins and one or more polymerizable ethylenically unsaturated monomers which process comprises subjecting said monomers to solution polymerization conditions in the presence of a homogeneous catalytic compound represented by the formula $LTi(NR^1_2)_3$ wherein L is a $_{II}$-bonded ligand selected from the group consisting of indenyl, $C_1$–$C_4$ alkyl substituted indenyl, —$OSiR_3$ substituted indenyl; R is a $C_1$–$C_4$ alkyl group; and each $R^1$ attached to a single nitrogen atom is the same, but can be different from the $R^1$ groups attached to a different nitrogen atom and is independently a $C_1$–$C_4$ alkyl group.

A further aspect of the present invention pertains to a process for polymerizing one or more monomers comprising one or more α-olefins or one or more α-olefins and one or more polymerizable ethylenically unsaturated monomers which process comprises subjecting said monomers to solution polymerization conditions in the absence of any cocatalyst or activator compound and in the presence of a homogeneous catalytic compound represented by the formula $LTi(NR^1_2)_3$ wherein L is a $_{II}$-bonded ligand selected from the group consisting of cyclopentadienyl, $C_1$–$C_4$ alkyl substituted cyclopentadienyl, oligomers of cyclopentadiene, $C_1$–$C_4$ alkyl substituted oligomers of cyclopentadiene, fluorenyl or $C_1$–$C_4$ alkyl substituted fluorenyl, and each $R^1$ attached to a single nitrogen atom is the same, but can be different from the $R^1$ groups attached to a different nitrogen atom and is independently a $C_1$–$C_4$ alkyl group.

DETAILED DESCRIPTION OF THE INVENTION

Definitions

The term oligomers of cyclopentadiene means those oligomers having from 10 to about 30 carbon atoms per molecule and any combination of such oligomers.

Catalysts where all of the R groups attached to any nitrogen atom are the same

The catalysts of the present invention represented by the formula $LTi(NR_2)_3$ wherein the $R^1$ groups are the same can be prepared by either of two independent methods.

In a first method, a titanium tetrakis(dialkylamide) represented by the formula $Ti(NR_2)_4$ wherein each R is independently a $C_1$ to $C_4$ alkyl group is reacted with indene or a substituted indene at a temperature from about −78° C. to about reflux, preferably from about 0° C. to about reflux temperature, more preferably combining the reagents at room temperature and then refluxing for a time sufficient to complete the reaction, usually from about 0.5 to about 48, preferably from about 1 to about 35, more preferably from about 5 to about 24, hours in the presence of a suitable solvent or reaction medium such as aliphatic or aromatic hydrocarbons or other such medium which is inert to either the reactants or reaction product. The preferred solvents are toluene, benzene, hexane, heptane, octane, isooctane, nonane, decane, kerosene, or any combination thereof and the like.

The desired product can be recovered from the reaction mixture by any suitable means such as removing volatile solvents or reaction media by vacuum distillation of the residue, if desired.

Higher reaction temperatures will require less time to complete the desired reaction whereas lower temperatures will require more time to complete the desired reaction; provided that the temperature is maintained below the decomposition temperature of any of the reactants or reaction products.

The solvent is chosen so that the reflux temperature of the reaction mixture does not exceed about 150° C.

In the foregoing preparation method, at temperatures below −78° C., the exchange reaction of the acidic proton of indene is slow and reaction yields are generally low within the described reaction time.

In the foregoing preparation method, at temperatures above about 150° C., many of the organometallic reactants will begin to undergo thermal decomposition.

In a second method, a titanium tris(dialkylamide)halide represented by the formula $XTi(NR^1{}_2)_3$ wherein $R^1$ and X are defined above is reacted with a metallated indene or substituted indene represented by the formula M(Ind)R' wherein M is an alkali metal such as Li, Na or K, and R' and Ind are as defined above at a temperature of from about −78° to about the reflux temperature, preferably from about 0° C. to about reflux temperature, more preferably by combining the reactants at room temperature (about 25° C.) and refluxing for a time sufficient to complete the reaction, usually from about 0.1 to about 12, preferably from about 0.2 to about 6, more preferably from about 0.5 to about 1, hours. The reaction is conducted in the presence of a suitable solvent or reaction medium which does not react with either the reactants or the reaction product. Suitable such solvents include, for example, aliphatic or aromatic hydrocarbons, glycol ethers or cyclic and acyclic ethers, combinations thereof and the like. Particularly suitable such solvents include, for example, pentane, hexane, toluene, benzene, diethylether, tetrahydrofuran, glyme, diglyme, dimethoxyethane, and the like. The most preferred solvent is diethylether. The desired reaction product(s) can be extracted from the reaction mixture with a suitable hydrocarbon such as pentane, hexane, heptane or toluene.

The desired product can be recovered from the reaction mixture by any suitable means such as filtering from the alkali metal salts, solvent extraction, decanting, or vacuum distillation, or any combination thereof and the like.

Higher reaction temperatures will require less time to complete the desired reaction whereas lower temperatures will require more time to complete the desired reaction; provided that the temperature is maintained below the decomposition temperature of the reactants or reaction products.

The solvent is chosen so that the reflux temperature of the reaction mixture does not exceed about 150° C.

In the foregoing preparation method, at temperatures below −78° C., the salt elimination reaction is slow and reaction yields are generally low within the described reaction time.

In the foregoing preparation method, at temperatures above about 150° C., many of the organometallic reactants will begin to undergo thermal decomposition.

Catalysts wherein all of the R groups attached to a single nitrogen atom are the same, but the R atoms attached to nitrogen atoms are different in at least two of the nitrogen atoms These catalysts of the present invention are prepared by different methods depending on the type of ligand employed and the number of different amide groups desired on the central metal ion.

In the first method, a dihalotitanium bis(dialkylamide) represented by the formula $X_2Ti(NR^1{}_2)_2$ wherein $R^1$ is a $C_1$–$C_4$ alkyl group and X is a halogen, preferably chlorine, bromine or iodine is reacted with a metallated indene or substituted indene represented by the formula M(Ind)R' wherein M is an alkali metal such as Li, Na or K, and R' is hydrogen, $C_1$–$C_4$ alkyl group, $-OSiR_3$, R is a $C_1$–$C_4$ alkyl group, and Ind is indene at a temperature of from about −100° C. to about the reflux temperature of the reaction mixture, preferably from about −78° C. to about reflux temperature, more preferably by combining the reactants at −78° C. and refluxing for a time sufficient to complete the reaction, usually from about 0.1 to about 12, preferably from about 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene. The product is then crystallized from a suitable solvent such as that used for extraction at reduced temperature or by reducing the solvent volume with the most preferred method being a combination of both techniques. The next step involves reaction of the indenyltitanium bis(dialkylamide)halide represented by the formula $(Ind)Ti(NR^1{}_2)_2X$ wherein $R^1$, X and Ind is defined as above with a metallated amide represented by the formula $M(NR^2{}_2)$ wherein M is an alkali metal selected such as Li, Na or K and $R^2$ is a $C_1$–$C_4$ alkyl group, each $R^2$ is the same but different from $R^1$ and is a $C_1$–$C_4$ alkyl group; at a temperature of from about −100° C. to about the reflux temperature of the reaction mixture, preferably from about −78° C. to about reflux temperature, more preferably by combining the reactants at −78° C. and refluxing for a time sufficient to complete the reaction, usually from about 0.1 to about 12 hours, preferably from 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene.

The desired product can be recovered from the reaction mixture by any suitable means such as filtering from the alkali metal salts, solvent extraction, decanting, vacuum distillation, or any combination thereof and the like.

Higher reaction temperatures will require less time to complete the desired reaction whereas lower temperatures will require more time to complete the desired reaction; provided that the temperature is maintained below the decomposition temperature of the reactants or reaction products.

The solvent is chosen so that the reflux temperature of the reaction mixture does not exceed about 150° C.

In the foregoing preparation method, at temperatures below −100° C. the salt elimination reaction is slow and reaction yields are generally low within the described reaction time.

In the foregoing preparation method, at temperatures above about 150° C. many of the organometallic reactants will begin to undergo thermal decomposition.

In the second method, a trihalotitanium dialkylamide represented by the formula $X_3Ti(NR^1{}_2)$ wherein $R^1$ is a $C_1$-$C_4$ alkyl group and X is a halogen such as chlorine, bromine or iodine is reacted with a metallated indene or substituted indene represented by the formula M(Ind)R' wherein M is an alkali metal such as Li, Na or K and R' is a hydrogen, $C_1$-$C_4$ alkyl group, —OSiR$_3$, R is a $C_1$-$C_4$ alkyl group, and Ind is indene at a temperature of from about −100° C. to about reflux temperature, preferably from about −78° C. to about reflux temperature, more preferably by combining the reactants at −78° C. and refluxing for a time sufficient to complete the reaction, usually from about 0.1 to about 12, preferably from about 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene. The product is then crystallized from a suitable solvent such as that used for extraction at reduced temperature or by reducing the solvent volume with the most preferred method being a combination of both techniques. The next step involves the reaction of the indenltitanium (dialkylamide)dihalide represented by the formula $R'(Ind)Ti(NR^1{}_2)X_2$ wherein R', $R^1$, X and Ind is defined as above with 2 equivalents of a metallated amide represented by the formula $M(NR^2{}_2)$ wherein M is an alkali metal such as Li, Na or K and $R^2$ is a $C_1$-$C_4$ alkyl group at a temperature of from about −100° C. to about the reflux temperature, preferably from about −78° C. to about reflux temperature, more preferably by combining the reactants at −78° C. and refluxing for a time sufficient to complete the reaction, usually from about 0.1 to about 12 hours, preferably from 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene.

The desired product can be recovered from the reaction mixture by any suitable means such as filtering from the alkali metal salts, solvent extraction, decanting, vacuum distillation, or any combination thereof and the like.

Higher reaction temperatures will require less time to complete the desired reaction whereas lower temperatures will require more time to complete the desired reaction; provided that the temperature is maintained below the decomposition temperature of the reactants or reaction products.

The solvent is chosen so that the reflux temperature of the reaction mixture does not exceed about 150° C.

In the foregoing preparation method, at temperatures below −100° C. the salt elimination reaction is slow and reaction yields are generally low within the described reaction time.

In the foregoing preparation method, at temperatures above about 150° C. many of the organometallic reactants will begin to undergo thermal decomposition.

In the third method a disproportionated dihalotitanium (dialkylamide) (dialkylamide') represented by the formula $X_2Ti(NR^1{}_2)(NR^2{}_2)$ wherein $R^1$ and $R^2$ are independently $C_1$-$C_4$ alkyl groups where each $R^1$ and each $R^2$ is the same, but each $R^1$ is different from each $R^2$, and X is a halogen, preferably chlorine, bromine or iodine is reacted with a metallated indene represented by the formula M(Ind)R' wherein M is an alkali metal such as Li, Na or K, and R' is hydrogen, a $C_1$-$C_4$ alkyl group, —OSiR3, and R is a $C_1$-$C_4$ alkyl group, and Ind is defined as indene at a temperature of from about −100° C. to about reflux temperature, preferably from about −78° C. to about reflux temperature, more preferably by combining the reactants at −78° C. and refluxing for a time sufficient to complete the reaction, usually from about 0.1 to about 12, preferably from about 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene. The product is then crystallized from a suitable solvent such as that used for extraction at reduced temperature or by reducing the solvent volume with the most preferred method being a combination of both techniques. The next step involves the reaction of the indenyltitanium (dialkylamide)(dialkylamide')halide represented by the formula $(Ind)Ti(NR^1{}_2)(NR^2{}_2)$ X wherein $R^1$, $R^2$ and Ind is defined as above with a metallated amide represented by the formula $M(NR^3{}_2)$ wherein M is an alkali metal such as Li, Na or K and $R^3$ is a $C_1$-$C_4$ alkyl group; and $R^1$, $R^2$ and $R^3$ are different but each $R^1$, each $R^2$ and each $R^3$ are the same; at a temperature of from about −100° C. to about the reflux temperature, preferably from about −78° C. to about reflux temperature, more preferably by combining the reactants at −78° C. and refluxing for a time sufficient to complete the reaction, usually from about 0.1 to about 12 hours, preferably from 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene.

The desired product can be recovered from the reaction mixture by any suitable means such as filtering from the alkali metal salts, solvent extraction, decanting, vacuum distillation, or any combination thereof and the like.

Higher reaction temperatures will require less time to complete the desired reaction whereas lower temperatures will require more time to complete the desired reaction provided that the temperature is maintained below the decomposition temperature of the reactants or reaction products.

The solvent is chosen so that the reflux temperature of the reaction mixture does not exceed about 150° C.

In the foregoing preparation method, at temperatures below $-100°$ C. the salt elimination reaction is slow and reaction yields are generally low within the described reaction time.

In the foregoing preparation method, at temperatures above about 150° C. many of the organometallic reactants will begin to undergo thermal decomposition.

In the fourth method a trihalotitanium dialkylamide represented by the formula $X_3Ti(NR^1_2)$ wherein $R^1$ is a $C_1$-$C_4$ alkyl group and X is a halogen atom such as chlorine, bromine or iodine is reacted with a metallated indene represented by the formula $M(Ind)R'$ wherein M is an alkali metal such as Li, Na or K and $R'$ is a hydrogen, $C_1$-$C_4$ alkyl group, —OSiR3 and Ind is defined as indene at a temperature of from about $-100°$ C. to about reflux temperature, preferably from about $-78°$ C. to about reflux temperature, more preferably by combining the reactants at $-78°$ C. and refluxing for a time sufficient to complete the reaction, usually from about 0.1 to about 12, preferably from about 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene. The product is then crystallized from a suitable solvent such as that used for extraction at reduced temperature or by reducing the solvent volume with the most preferred method being a combination of both techniques. The next step involves reaction of the indenyltitanium (dialkylamide)dihalide represented by the formula $(Ind)Ti(NR^1_2)X_2$ wherein $R^1$, X and Ind is defined as above with a metallated amide represented by the formula $M(NR^2_2)$ wherein M is an alkali metal such as Li, Na of K and $R^2$ is a $C_1$-$C_4$ alkyl group and each $R^1$ and each $R^2$ are the same but $R^1$ and $R^2$ are different at a temperature of from about $-100°$ C. to about the reflux temperature, preferably from about $-78°$ C. to about reflux temperature, more preferably by combining the reactants at $-78°$ C. and refluxing for a time sufficient to complete the reaction, usually from about 0.1 to about 12 hours, preferably from 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene or the product need not be isolated for the next reaction step. The next step involves reaction of indenyltitanium (dialkyl$^1$amide)(dialkyl$^2$amide)halide represented by the formula $(Ind)Ti(NR^1_2)(NR^2_2)X$ wherein $R^1$, $R^2$, X and Ind is defined as above with a metallated amide represented by the formula $M(NR^3_2)$ wherein M is an alkali metal selected from the group Li, Na or K, R is a $C_1$-$C_4$ alkyl group, and each $R^3$ is a $C_1$-$C_4$ alkyl group different from $R^1$ and $R^2$ at a temperature of from about $-100°$ C. to about the reflux temperature, preferably from about $-78°$ C. to about reflux temperature, more preferably by combining the reactants at $-78°$ C. and refluxing for a time sufficient to complete the reaction, usually from about 0.1 to about 12 hours, preferably from 0.2 to about 6, more preferably from about 0.5 to about 1 hours. The reaction is conducted in the presence of a suitable solvent or reaction medium which does not react with either the reactants or the reaction product. Suitable solvents include, for example, aliphatic or aromatic hydrocarbons, glycol ethers or cyclic and acyclic ethers, combinations thereof and the like. Particularly suitable solvents include, for example, pentane, hexane, toluene, benzene, diethyl ether, tetrahydrofuran, glyme, diglyme, dimethoxyethane, and the like. The most preferred solvent is diethyl ether. The desired reaction product can be extracted from the reaction mixture with a suitable hydrocarbon such as pentane, hexane, heptane, benzene or toluene.

The desired product can be recovered from the reaction mixture by any suitable means such as filtering from the alkali metal salts, solvent extraction, decanting, vacuum distillation, or any combination thereof and the like.

Higher reaction temperatures will require less time to complete the desired reaction whereas lower temperatures will require more time to complete the desired reaction; provided that the temperature is maintained below the decomposition temperature of the reactants or reaction products.

The solvent is chosen so that the reflux temperature of the reaction mixture does not exceed about 150° C.

In the foregoing preparation method, at temperatures below $-100°$ C. the salt elimination reaction is slow and reaction yields are generally low within the described reaction time.

In the foregoing preparation method, at temperatures above about 150° C. many of the organometallic reactants will begin to undergo thermal decomposition.

It is generally understood that several reaction products are obtained due to side reactions when preparing complexes involving two dialkylamide ligands in which the alkyl group is n-propyl or n-butyl. Also, many products are observed in the preparation of complexes containing three different dialkylamide groups. These are generally reactions due to reductive elimination of the halide from the transition metal which is not followed by oxidative addition of the amide group. It is evident, spectroscopically, that paramagnetic components are present in the reaction mixtures indicating that reductive elimination occurs.

Particularly suitable catalysts wherein the $\pi$-bonded ligand is indenyl or substituted indenyl which can be employed herein, include, for example, indenyltitanium tris(dimethylamide), indenyltitanium tris(diethylamide), indenyltitanium tris(di-n-propylamide), indenyltitanium tris(di-n-butylamide), indenyltitanium bis(dimethylamide) (diethylamide), indenyltitanium bis(dimethylamide) (di-n-propylamide), indenyltitanium bis(dimethylamide) (di-n-butylamide) indenyltitanium bis(dimethylamide) (dimethylamide), indenyltitanium bis(dimethylamide) (di-n-propylamide), indenyltitanium bis(dimethylamide) (di-n-butylamide), indenyltitanium bis(di-n-propylamide) (dimethylamide), indenyltitanium bis(di-n-propylamide) (diethylamide), indenyltitanium bis(di-n-propylamide) (di-n-butylamide), indenyltitanium bis(di-n-butylamide) (dimethylamide), indenyltitanium bis(di-n-butylamide) (diethyamide), indenyltitanium bis(di-n-butylamide) (di-n-propylamide), indenyltitanium (dimethylamide) (diethyamide) (di-n-propylamide), indenyltitanium (diethylamide) (di-n-propylamide) (di-n-butylamide), indenyltitanium (dimethylamide) (di-n-propylamide) (di-n-butylamide), indenyltitanium (dimethylamide) (diethylamide) (di-n-butylamide), any combination thereof and the like.

Particularly suitable catalysts wherein the $\pi$-bonded ligand is cyclopentadienyl or $C_1$-$C_4$ substituted cyclopentadienyl or oligomer of cyclopentadiene or $C_1$-$C_4$ substituted oligomer of cyclopentadiene which can be employed herein include, for example, cyclopentadienyltitanium tris(dimethylamide), cyclopentadienyltitanium tris(diethylamide), cyclopentadienyltitanium tris(di-n-propylamide), cyclopentadienyltitanium tris(di-n-butylamide), methylcyclopentadienyltitanium tris(dimethylamide), methylcyclopentadienyltitanium tris(diethylamide), methylcyclopentadienyltitanium tris(di-n-propylamide), methylcyclopentadienyltitanium tris(di-n-butylamide), pentamethylcyclopentadienyltitanium tris(dimethylamide), pentamethylcyclopentadienyltitanium tris(diethylamide), pentamethylcyclopentadienyltitanium tris(di-n-propylamide), pentamethylcyclopentadienyltitanium tris(di-n-butylamide), any combination thereof and the like.

Particularly suitable catalysts wherein the $\pi$-bonded ligand is fluorenyl or $C_1$-$C_4$ substituted fluorenyl include, for example, fluorenyltitanium tris(dimethylamide), fluorenyltitanium tris(diethylamide), fluorenyltitanium tris(di-n-propylamide), fluorenyltitanium tris(di-n-butylamide), any combination thereof and the like.

Suitable $\alpha$-olefins which can be employed herein include, for example, those having from 2 to about 20, preferably from 2 to about 10, more preferably from 2 to about 8 carbon atoms. Particularly suitable such $\alpha$-olefins include, for example, ethylene, propylene, butene-1, pentene-1, hexene-1, 4-methyl-pentene-1, heptene-1, octene-1, nonene-1, decene-1, undecene-1, tridecene-1, tetradecene-1, 3-methylbutene-1, any combination of any two or more and the like monomers which do not destroy the catalyst.

Suitable polymerizable ethylenically unsaturated monomers which can be copolymerized with any one or more of the aforementioned $\alpha$-olefins include, for example, dienes; ethylenically unsaturated nitriles; unsaturated aliphatic or halogen substituted aromatic compounds; any combination of any two or more such polymerizable monomers and the like. Particularly suitable such polymerizable ethylenically unsaturated monomers include, for example, butadiene, neoprene, isoprene, chloroprene, 1,7-octadiene, 1,4-hexadiene, acrylonitrile, methacrylonitrile, styrene, 4-methyl styrene, chlorostyrene, bromostyrene, any combination of any two or more such polymerizable monomers and the like.

The catalyst wherein the $\pi$-bonded ligand is indenyl or substituted indenyl can be employed in conjunction with a cocatalyst or activator compound, if desired, although such cocatalyst or activator compound is not required. Suitable such cocatalysts or activator compounds include, for example, methylaluminoxane.

When these cocatalysts or activator compounds are employed, they are employed in amounts which provide an atomic ratio of the metal present in the cocatalyst or activator compound to Ti of from about 0.001:1 to about 10,000:1, preferably from about 0.01:1 to about 5,000:1, more preferably from about 0.1:1 to about 1,000:1.

When employed, the cocatalyst or activator compound can be mixed with the titanium-containing catalyst prior to being introduced into the polymerization reactor or the cocatalyst or activator compound and the titanium-containing catalyst can be added separately to the polymerization reactor.

The polymerization can be conducted under slurry, solution or gas phase conditions.

The polymerization process can be conducted at temperatures of from about 0° C. to about 250° C., preferably from about 25° C. to about 200° C., more preferably from about 40° C. to about 170° C. For polymerization under solution conditions, the temperature is usually in the range of from about 120° C. to about 250° C., preferably from about 130° C. to about 200° C., more preferably from about 140° C. to about 170° C. For polymerization under slurry conditions, the temperature is usually in the range of from about 0° C. to about 100° C., preferably from about 25° C. to about 95° C., more preferably from about 50° C. to about 90° C.

The polymerization process can be conducted at pressures of from about 5 psig (0.17 kg/m$^2$) to about 10,000 psig (399 kg/m$^2$), preferably from about 50 psig (1.7 kg/m$^2$) to about 1,000 psig (33.9 kg/m$^2$), more preferably from about 100 psig (3.39 kg/m$^2$) to about 700 psig (23.73 kg/m$^2$).

Suitable diluents which can be employed as the polymerization medium in the solution process for polymerizing $\alpha$-olefins include, for example, liquified aliphatic hydrocarbons having from about 2 to about 15, preferably from about 4 to about 12, more preferably from about 6 to about 10, carbon atoms; aromatic or alkyl substituted aromatic hydrocarbons having from about 6 to about 12 carbon atoms; any combination thereof and the like.

The polymerization can be conducted in the presence of hydrogen or other known molecular weight control methods such as comonomer concentration, reactor temperature, monomer/solvent ratio, any combination thereof and the like. These molecular weight control methods are employed in functionally equivalent amounts, i.e. those amounts which will result in the polymer having the desired molecular weight or melt index or melt flow rate values, which values are indicative of relative molecular weights i.e. the higher the melt index value, the lower the molecular weight.

The following examples are illustrative of the present invention, but are not to be construed as to limiting the scope thereof in any manner.

GENERAL PROCEDURES

The following practices and procedures are common to all preparative examples:

All complexes are prepared under dry nitrogen which is passed through a column of reduced chromium on silica to remove the last traces of water and oxygen. Hexane and diethyl ether are distilled from the Na/K benzophenone ketal radical anion under nitrogen. Toluene is distilled from either Na or Na/K alloy under nitrogen. All solvents are degassed prior to use. Manipulations are performed using standard Schlenk and vacuum line techniques.

n-Butyllithium, titanium tetrachloride and indene are purchased from Aldrich Chemical Co. and used without further purification. Diethylamine and dipropylamine are purchased from Aldrich Chemical Co. and are purified by refluxing and distilling from CaH$_2$ under dry nitrogen. Dimethylamine (anhydrous) is purchased from Matheson and used without further purification. Methylaluminoxane (MAO) is purchased from Schering. Methylcyclopentadiene is obtained from the Chemical Sample Company and is distilled prior to use. Cyclopentadiene is obtained from The Dow Chemical Company. The complexes titanium tetrakis(dimethylamide), titanium tetrakis(diethylamide) and titanium tetrakis(dipropylamide) are prepared in the following manner.

PREPARATION OF TITANIUM TETRAKIS(DIALKYLAMIDES)

A. Preparation of titanium tetrakis(dimethylamide)
Step (1) Preparation of lithium dimethylamide.

Dimethylamine is condensed into a 250 mL Schlenk flask at −20° C. over Linde 4A molecular sieves. The liquid is maintained at or below −10° C. to avoid vapor phase transition. A 1 liter Schlenk flask is charged with 350 mL of diethyl ether and fitted with a pressure equalizing dropping funnel and magnetic stir bar. The contents are cooled in a dry ice/acetone bath and maintained at or below −20° C. for all additions. To the chilled diethyl ether in the 1000 mL flask is added n-butyllithium, 0.500 mole of 2.90 M solution in hexane. Diethyl ether, 150 mL, is added to the dropping funnel which is jacketed with dry ice to maintain a liquid temperature below −20° C. followed by excess dimethylamine, 35 mL (0.528 mole). The dimethylamine is slowly dripped into the 1000 mL Schlenk flask over the course of one hour. A suspension of white pyrophoric powder is obtained which is determined to be lithium dimethylamide. The mixture is warmed to room temperature for one hour to devolatilize excess dimethylamine.

Step (2) Preparation of titanium tetrakis(dimethylamide)

The same apparatus described in Step (1) of Example A is used in this procedure. The 250 mL pressure equalizing dropping funnel is charged with 100 mL of toluene and titanium tetrachloride, 12.4 mL (0.112 mole). The solution is added dropwise to the magnetically stirred suspension of lithium dimethylamide over the course of 0.5 hour at −20° C. A brown solution over insoluble lithium salts is obtained which is refluxed two hours. All volatiles are removed under vacuum at room temperature and the mixture is extracted twice with 200 mL portions of hexane. The salts are filtered from the solution and the extracts are combined. Solvent is distilled from the solution to give a dark orange oil. Distillation of the oil (boiling point=60° C.−63° C.@0.025 mm Hg) gives the orange liquid titanium tetrakis(dimethylamide) in 90% yield.

B. Preparation of titanium tetrakis(diethylamide)
Step (1) Preparation of lithium diethyamide.

To a 500 mL Schlenk flask is added 250 mL of diethyl ether which is chilled in a dry ice/acetone bath to −78° C. Next is added n-butyllithium, 0.300 mole of 2.90 M solution in hexane, and the contents are allowed to warm to −20° C. Diethylamine, freshly distilled from calcium hydride, 35 mL (0.34 mole), is added via a 250 mL pressure equalizing dropping funnel over the course of 30 minutes while stirring the mixture at −20° C. The contents are warmed to room temperature for one hour.

Step (2) Preparation of titanium tetrakis(diethylamide)

The same apparatus described in Step (1) of Example B is used in this procedure. The 250 mL dropping funnel is charged with 50 mL of toluene and titanium tetrachloride, 7.7 mL (75 mmole), and added to the solution of lithium diethylamide which is chilled to −78° C. over the course of 30 minutes. The mixture is warmed to room temperature then refluxed two hours. All volatiles are removed under vacuum and the residue is extracted twice with 100 mL portions of hexane and filtered from the lithium salts. The combined extracts are reduced in solvent volume then transferred to a small scale distillation apparatus. The complex titanium tetrakis(diethylamide) is distilled from the mixture at 103°–105° C. (0.025 mm Hg) to give approximately 8 g as an orange liquid.

C. Preparation of titanium tetrakis(di-n-propylamide)
Step (1) Preparation of lithium di-n-propylamide.

A 1 L Schlenk flask is equipped with a 250 mL pressure equalizing dropping funnel and magnetic stir bar is charged with 500 mL of diethyl ether. The contents are chilled to −78° C. in a dry ice/acetone bath and n-butyllithium, 0.250 mole of a 2.81M solution in hexane, is next added. A solution containing dipropylamine, 38 mL (0.277 mole), dissolved in 150 mL of diethyl ether is added dropwise to the n-butyllithium solution while the contents are stirred magnetically and allowed to slowly warm to room temperature. The contents are stirred overnight at room temperature to insure complete reactions.

Step (2) Preparation of titanium tetrakis(di-n-propylamide)

The same apparatus described in Step (1) of Example C is used in this procedure. The 250 mL dropping funnel is charged with toluene, 100 mL, and titanium tetrachloride, 10.7 g (0.0562 mole). This is added dropwise to the flask containing lithium di-n-propylamide while stirring magnetically. Total additions times are typically 30 minutes. The mixture is refluxed for 1.5 hours. All volatiles are removed by distillation and under vacuum to give a deeply colored brown, oily residue. The residue is extracted with hexane, 2×150 mL, then filtered from the lithium salts. The extracts are combined and solvent is removed under vacuum. The remaining oil is transferred to a small scale distillation apparatus. Vacuum distillation at 157° C. and 0.05 mm Hg gave the product as an orange-brown liquid, titanium tetrakis(dipropylamide).

Complexes are stored below −20° C. for liquids or in an inert atmosphere box under nitrogen depending on thermal stability. Solids are stored in an inert atmosphere box under dry nitrogen. Polymerization compositions are diluted or mixed in a Vacuum Atmospheres dry box equipped with a recirculating catalyst train packed with 13× molecular sieves and a deoxygenation catalyst such as those available from Vacuum Atmospheres.

In the following examples, the melt index values $I_2$ and $I_{10}$ are determined by ASTM D 1238-86, condition "E" for $I_2$ and condition "N" for $I_{10}$, and the density values are determined by ASTM D 1248-84.

EXAMPLE 1

A. Preparation of indenyltitanium tris(dimethylamide), (Complex IA)

A 250 mL Schlenk flask is charged with toluene, 75 mL, and titanium tetrakis(dimethylamide), 2.35 g (10.48 mmole). The mixture is stirred magnetically throughout the procedure. Freshly degassed indene (nitrogen sparged) is added to the Schlenk flask at room temperature in excess, 2.44 mL (20.96 mmole). The mixture is refluxed at least 24 hours giving a blood red solution. All volatiles are removed under vacuum at room temperature leaving a deep red, oily residue. The residue is transferred in a minimum of hexane to a micro scale distillation apparatus and distilled under vacuum. A viscous red oil distills at 60° C. (0.025 mm Hg) which is identified by nuclear magnetic resonance (NMR) as indenyltitanium tris(dimethylamide). The yield is 70% by this method of preparation.

B. Preparation of indenyltitanium tris(dimethylamide), (Complex IB)

Step (1): Preparation of chlorotitanium tris(dimethylamide).

The disproportionation product of titanium tetrakis(dimethylamide) with titanium tetrachloride is prepared in the following manner. A 250 mL Schlenk flask is charged with titanium tetrakis(dimethylamide), 7.74 g (34 mmole) and toluene, 100 mL. To the magnetically stirred mixture is added titanium tetrachloride, 2.18 g (12 mmole). The mixture is refluxed at least 1 hour resulting in a deep brown solution. All volatiles are removed under vacuum at room temperature leaving a yellow-brown powder. The powder is transferred in a dry box to a sublimation apparatus then heated under vacuum (0.05 mmHg). Yellow needles of chlorotitanium tris(dimethylamide) sublimed onto a dry ice cooled probe between 50° and 70° C. Crystals are removed from the probe in a dry box and transferred to bottles for storage. The yield is 84% for this preparation.

Step (2): Preparation of lithium indenide.

A 100 mL Schlenk flask is charged with diethyl ether, 50 mL, and n-butyllithium, 5.2 mL (13.88 mmole) of a 2.68M solution in hexane) at −78° C. To the magnetically stirred, chilled solution is added nitrogen degassed indene, 1.8 mL (15.27 mmole). The mixture is stirred and warmed to room temperature over 1 to 2 hours. The mixture is stirred at least an additional 4 hours at room temperature to insure complete reaction prior to further use.

Step (3): Reaction of lithium indenide with chlorotitanium tris(dimethylamide).

A 250 mL Schlenk flask is charged with chlorotitanium tris(dimethylamide), 2.72 g (12.62 mmole), and diethylether, 75 mL. The flask is chilled to −78° C. and stirred magnetically while adding the solution containing lithium indenide (Step 2 of Example 1B). The mixture is warmed to room temperature then refluxed approximately 1.5 hours. All volatiles are removed under vacuum at room temperature leaving a deep red oily residue. The residue is extracted with hexane (1×50 mL) and the extract is filtered from the LiCl salts. All volatiles are removed under vacuum at room temperature leaving a viscous red oil. A proton NMR of the oil shows the product is sufficiently pure indenyltitanium tris(dimethylamide) and is used without further purification. Test for chloride shows it to be absent from the product. The yield is 95% for this preparative method.

C. Preparation of indenyltitanium tris(diethylamide). (Complex II)

Step (1): Preparation of chlorotitanium tris(diethylamide).

A 250 mL Schlenk flask is charged with toluene, 100 mL, and titanium tetrakis(diethylamide), 6.21 g (18.5 mmole). To the magnetically stirred solution is added titanium tetrachloride, 1.17 g (6.15 mmole) resulting in a gradual darkening of the solution. The mixture is stirred 1 hour while refluxing. All volatiles are removed under vacuum at room temperature leaving a yellow-brown oil. The oil is transferred to a micro distillation apparatus and distilled under vacuum. A yellow-brown liquid is obtained which distills at 112° to 118° C. (at 0.025 mm Hg). The product is determined to be chloro titanium tris(diethylamide).

Step (2): Preparation of lithium indenide.

A 250 mL Schlenk flask is charged with diethyl ether, 100 mL, then chilled to −20° C. To the chilled solvent is added n-butyllithium, 5.4 mL of a 2.79M in hexane (15 mmole). To the magnetically stirred mixture is added nitrogen degassed indene, 1.92 mL (16.5 mmole). The mixture is stirred overnight at room temperature.

Step (3): Reaction of lithium indenide with chlorotitanium tris(diethylamide).

To a 100 mL Schlenk flask outfitted with a magnetic stir bar is added, in a dry box, chorotitanium tris(diethylamide), 4.05 g (13.5 mmole). The flask is transferred to a vacuum line and toluene, 50 mL, is added and the solution is stirred to dissolve all of the solid. The solution containing ClTi(NEt$_2$)$_3$ is transferred via canula on a vacuum line to the flask containing lithium indenide prepared in diethyl ether as described in Step (2) of Example 1C above. The mixture is refluxed 4 hours giving a deep yellow solution. All volatiles are removed under vacuum at room temperature leaving a darkly colored oil. The oil is extracted with hexane (1×50 mL) and the light yellow solid is allowed to separate from the red solution. Solvent is removed under vacuum leaving a deep red, viscous oil. An NMR is obtained of the oil which indicates the complex is pure indenyltitanium tris(diethylamide), therefore, it is used without further purification.

D. Preparation of indenyltitanium tris(di-n-propylamide). (Complex III)

Step (1): Preparation of chlorotitanium tris(di-n-propylamide).

A 250 mL Schlenk flask equipped with a magnetic stir bar is charged with titanium tetrakis(di-n-propylamide), 4.49 g (10.0 mmole), and toluene, 100 mL. Titanium tetrachloride, 0.63 g (3.34 mmole), is diluted in toluene, 50 mL, in a 100 mL Schlenk flask then added to the magnetically stirred flask containing titanium tetrakis(di-n-propylamide). The darkly colored solution is refluxed one hour then all volatiles are removed under vacuum. The product, chlorotitanium tris(di-n-propylamide) is used without further purification.

Step (2): Preparation of lithium indenide.

A 100 mL Schlenk flask is charged with diethyl ether, 50 mL, and n-butyllithium, 5.22 mL (14.67 mmole) of a 2.81M solution in hexane, at −78° C. To the magnetically stirred, chilled solution is added nitrogen degassed indene, 1.70 g (14.6 mmole). The mixture is stirred and warmed to room temperature over 1 to 2 hours. The solution is stirred at least an additional 4 hours at room temperature to insure complete reaction prior to further use.

Step (3): Reaction of lithium indenide with chlorotitanium tris(di-n-propylamide).

To a 250 mL Schlenk flask is added chlorotitanium tris(di-n-propylamide), 6.18 g (13.34 mmole), in diethyl ether, 100 mL. Lithium indenide, 14.67 mmole, in diethyl ether is next added to the magnetically stirred solution containing the titanium complex. The reactants are combined at −20° C. then allowed to warm to room temperature and stirred at least 12 hours. The mixture is refluxed for 45 minutes. All volatiles are removed under vacuum at room temperature. A deeply colored oily residue remained. The residue is extracted with hexane, 1×50 mL, giving a blood red solution over white salts. Hexane is removed under vacuum leaving a darkly colored, viscous oil. The extract is placed under vacuum an additional 8 hours at 50° C. ($1 \times 10^{-6}$ Torr) to remove unreacted indene. An NMR obtained of the residue indicates the material is sufficiently pure indenyltitanium tris(di-n-propylamide), Complex III and is used without further purification.

E. Preparation of cyclopentadienyltitanium tris(dimethylamide). (Complex IV)

A 250 mL Schlenk flask is charged with titanium tetrakis(dimethylamide), 2.48 g (11.06 mmole), and toluene, 100 mL. Freshly cracked cyclopentadiene monomer, 2.7 mL (33.18 mmole), is added to the magnetically stirred solution. The mixture is refluxed 1 hour giving a deep red solution. All volatiles are removed under vacuum at room temperature leaving a viscous deep red oil. The oil is transferred to a microdistillation apparatus and a low melting solid is distilled at 70° C. under vacuum (0.05 mm Hg). The product is determined to be cyclopentadienyltitanium tris(dimethylamide).

F. Preparation of methylcyclopentadienyltitanium tris(dimethylamide). (Complex V)

A 250 mL Schlenk flask is charged with titanium tetrakis(dimethylamide), 3.73 g (16.64 mmole), and toluene, 100 mL. Methylcyclopentadiene, 5.33 g (66.54 mmole), is added to the magnetically stirred solution. The mixture is refluxed 1.5 hours. Solvent and volatiles are removed under vacuum leaving a brown residue. The residue is transferred to a microdistillation apparatus and a forerun of titanium tetrakis(dimethylamide) is distilled from the mixture (at 35°–40° C. and 0.025 mm Hg) followed by a red low melting solid (at 104°–108° C. and 0.025 mm Hg) which is determined to be methylcyclopentadienyltitanium tris(dimethylamide) by proton NMR.

EXAMPLE 2

POLYMERIZATION

Following is the method employed for the polymerization reaction and is used in all examples in Table I with the exception as noted for the low temperature runs. A stirred, one gallon (3.79 liter) batch reactor containing two liters of ISOPAR ™ E (a fractionated isoparaffinic solvent having a boiling range of 113°–143° C. available from Exxon Company USA, a division of Exxon Corporation) and optionally a comonomer, is heated to the desired polymerization temperature and the solvent vapor pressure recorded. To this an amount of hydrogen is optionally added which is recorded as the differential pressure drop from a 75 mL pressurized tank. The reactor is then pressurized with ethylene to give the final desired reactor pressure which is approximately 450 psig (3.10 MPa). An amount of catalyst is injected into the reactor determined by the total amount of product desired over time or until the catalyst is no longer active. For solution conditions the amount of catalyst injected or duration of the polymerization run is limited to avoid conditions in which the polymer precipitates from the solution phase. Ethylene reactor pressure is maintained at a constant level by a demand feed regulator to replace the ethylene consumed by the polymerization reaction. The total reaction time is held constant or varied based on desired yields of polymer. The results are given in Table I.

EXAMPLE 3

A. Preparation and activation of catalyst mixtures containing MAO cocatalyst.

Some examples containing MAO (methylaluminoxane) are prepared for polymerization as follows. The ratio of titanium (Ti) to aluminum (Al) is prepared as described using the appropriate volume of each component. The MAO and Ti complex are combined in 4 oz (118 mL) catalyst bottles in a dry box prior to injection into the batch reactor.

(1) A stock solution of indenyltitanium tris(dimethylamide), complex IA, is prepared by dissolving 0.5 mmole in ISOPAR ™ E, 50 mL. To a 50 mL syringe is added 2.5 mL of the stock solution containing complex I, indenyltitanium tris(dimethylamide), and 50 mL of a 0.33M solution of MAO cocatalyst. (Atomic ratio of Al:Ti=1000:1)

(2) To a 50 mL syringe is added 3 mL of the stock solution from Example 3A-1 containing complex IA, indenyltitanium tris(dimethylamide), and 36 mL of a 0.33M solution of MAO cocatalyst. (Atomic ratio of Al:Ti=400:1)

(3) To a 10 mL syringe is added 4 mL of the stock solution from Example 3A-1 containing complex IA, indenyltitanium tris(dimethylamide), and 5 mL of a 0.33M solution of MAO cocatalyst. (Atomic ratio of Al:Ti=50:1)

B. Preparation of nonactivated catalyst compositions.

An amount of catalyst is dissolved in ISOPAR ™ E to give a known concentration of the transition metal complex. An aliquot is injected in the reactor based on the formulated concentration to give the appropriate amount of transition metal complex expressed in μmole of Ti. The concentration of the complex in the inert diluent (ISOPAR ™ E) is completely arbitrary and not critical to catalyst preparation. The only consideration should be the volume of the injection pressure vessel which should accommodate the entire aliquot. Concentrations are adjusted to insure that the entire aliquot(s) of the catalyst component(s) are accommodated by the injection pressure vessel.

(1) 5 mL of a 0.01M solution of catalyst complex is injected into the reactor.
(2) 5 mL of a 0.005M solution catalyst complex is injected into the reactor.
(3) 0.009 g (30 μmole) of complex IA (indenyltitanium tris(dialkylamide)) is dissolved in approximately 10 mL ISOPAR ™ E and injected into the reactor.
(4) 20 mL of a 0.001M solution of catalyst complex is injected into the reactor.
(5) A 0.001M solution of complexes IB (indenyltitanium tris(dialkylamide)) and II (indenyltitanium tris(diethylamide)) are prepared and 20 mL of the blend is injected into the reactor.
(6) 10 mL of a 0.01M solution of catalyst complex is injected into the reactor.
(7) A 0.002M solution of complexes IB (indenyltitanium tris(dimethylamide)) and III (indenyltitanium tris(dipropylamide)) are prepared and 10 mL of each solution are blended in a 4 oz (118 mL) bottle. 20 mL of the blend is injected into the reactor.

The results are given in Table I.

TABLE I

| | Run Designation | | | | |
|---|---|---|---|---|---|
| | A* | B* | C* | D | E |
| Source of Complex, Ex. | 1A | 1A | 1A | 1A | 1A |
| Ratio of $I^a:II^b:III^c$ | 1:0:0 | 1:0:0 | 1:0:0 | 1:0:0 | 1:0:0 |
| Cat. Prep., Ex. | 3A1 | 3A2 | 3A3 | 3B1 | 3B1 |
| Comonomer, | | | | | |
| Type | octene | octene | octene | octene | None |
| mL | 345 | 345 | 345 | 345 | — |
| Reactor Temp., °C. | 150 | 150 | 150 | 150 | 150 |
| $\Delta H_2$, | | | | | |
| psig | 50 | 100 | 50 | 50 | 100 |
| kPa | 344.7 | 689.5 | 344.7 | 344.7 | 689.5 |
| Ti, μmole | 25 | 30 | 40 | 50 | 50 |
| Run Time, min. | 10 | 20 | 10 | 10 | 10 |
| Eff. kgPE/g-Ti | 12 | 9 | 11 | 27 | 26 |
| Melt Index$^d$, | | | | | |
| $I_2$ | ND$^f$ | ND$^f$ | ND$^f$ | 5.81 × | 2.52 × |
| $I_{10}$ | ND$^f$ | ND$^f$ | ND$^f$ | $10^{5.8}$ | $10^{4.8}$ |
| Mol. Wt. Dist., | ND$^f$ | ND$^f$ | ND$^f$ | 8.2$^h$ | ND$^f$ |
| $I_{10}/I_2$ | ND$^f$ | ND$^f$ | ND$^f$ | | |
| Density$^e$ | ND$^f$ | ND$^f$ | ND$^f$ | 0.9211 | ND$^f$ |

| | Run Designation | | | | |
|---|---|---|---|---|---|
| | F | G | H* | I* | J$^i$ |
| Source of Complex, Ex. | 1A | 1A | 1E | 1F | 1A |
| Ratio of $I^a:II^b:III^c$ | 1:0:0 | 1:0:0 | — | — | 1:0:0 |
| Cat. Prep., Ex. | 3B1 | 3B1 | 3B6 | 3B2 | 3B3 |
| Comonomer, | | | | | |
| Type | octene | octene | octene | octene | None |
| mL | 345 | 345 | 345 | 345 | — |
| Reactor Temp., °C. | 175 | 140 | 140 | 150 | 80 |
| $\Delta H_2$, | | | | | |
| psig | 100 | 100 | 100 | 100 | 10$^j$ |
| kPa | 689.5 | 689.5 | 689.5 | 689.5 | 68.9 |
| Ti, μmole | 50 | 50 | 100 | 25 | 30 |
| Run Time, min. | 10 | 25 | 10 | 15 | 60 |
| Eff. kgPE/g-Ti | 11 | 35 | 0.4 | 11 | 13 |
| Melt Index$^d$, $I_2$ | ND$^f$ | ND$^f$ | ND$^f$ | ND$^f$ | ND$^f$ |
| $I_{10}$ | | | | | |
| Mol. Wt. Dist., | ND$^f$ | ND$^f$ | ND$^f$ | ND$^f$ | ND$^f$ |
| $I_{10}/I_2$ | | | | | |
| Density$^e$ | ND$^f$ | ND$^f$ | ND$^f$ | 0.9497 | 0.9501 |

TABLE I-continued

| | Run Number | | | |
|---|---|---|---|---|
| | K | L | M | N |
| Source of Complex, Ex. | IC | ID | IB, IC | IB, IC, ID |
| Ratio of $I^a:II^b:III^c$ | 0:1:0 | 0:0:1 | .5:.5:0 | 0.3:0.3:0.3 |
| Cat. Prep., Ex. | 3B4 | 3B4 | 3B5 | 3B7 |
| Comonomer, | | | | |
| Type | octene | None | octene | octene |
| mL | 345 | — | 345 | 345 |
| Reactor Temp., °C. | 150 | 150 | 150 | 150 |
| $\Delta H_2$, | | | | |
| psig | 100 | 100 | 25 | 100 |
| kPa | 689.5 | 689.5 | 172.4 | 689.5 |
| Ti, μmole | 20 | 20 | 20 | 40 |
| Run Time, min. | 10 | 15 | 15 | 14.3 |
| Eff. kgPE/g-Ti | 60 | 116 | 36 | 25 |
| Melt Index$^d$, | | | | |
| $I_2$ | ND$^f$ | 1.4 | 16.95 | 27.06 |
| $I_{10}$ | | 11.9 | 97.65 | 210.8 |
| Mol. Wt. Dist., $I_{10}/I_2$ | ND$^f$ | 8.51 | 5.76 | 7.79 |
| Density$^e$ | ND$^f$ | 0.9627 | ND$^f$ | 0.9463 |

*Not an example of the present invention.
$^a$IA and IB are indenyltitanium tris(dimethylamide).
$^b$II is indenyltitanium tris(diethylamide).
$^c$III is indenyltitanium tris(propylamide).
$^d$Melt index is determined by ASTM D 1238-86, condition "E" for $I_2$ and condition "N" for $I_{10}$.
$^e$Density is determined by ASTM D 1248-84.
$^f$Not determined.
$^g$Weight average molecular weight by gel permeation chromatography (GPC) on a Waters 150-C ALC/GPC using 3 Polymer Laboratories, Ltd. PLgel 10 μm mixed 300 × 7, 5 mm columns in series.
$^h$Ratio of Mw/Mn as determined by GPC.
$^i$A 450 mL stainless steel Parr reactor is used for this run. This is approximately 0.1 the scale of the 1 gallon batch reactors employed for the other runs. Solvent volume in the reactor is 250 mL
$^j$Hydrogen pressure determined by the increase in gauge pressure before and after admitting hydrogen to the reactor.

PREPARATION OF MIXED TRIS(DIALKYLAMIDO)INDENYLTITANIUM COMPLEXES

EXAMPLE 4

A. Preparation of indenyltitanium bis(dimethylamide) diethylamide, VI.

Step (1) Preparation of dichlorotitanium bis(dimethylamide).

A 250 mL Schlenk flask is charged with toluene, 150 mL, and titanium tetrakis(dimethylamide), 6.994 g (31.2 mmole). To the magnetically stirred mixture is added titanium tetrachloride, 5.92 g (31.2 mmole). The solution changes color immediately to a deep brown color. The mixture is refluxed with stirring approximately one hour. All volatiles are removed under vacuum (0.0025 mm Hg) horizontally. The product is brown needles which sublimes at 55°-60° C. which corresponds to the properties observed by E. Benzing and W. Kornicker in Chem. Ber., vol. 94, pp 2263-2267 (1961) for $Cl_2Ti(NMe_2)_2$. Product yield is 10.69 g (53.0 mmole, 85%).

Step (2) Preparation of lithium indenide.

A 500 mL Schlenk flask is charged with diethyl ether, 225 mL, and n-butyllithium, 13.6 mL of a 2.93M solution in hexane (45 mmole). The mixture is stirred magnetically and chilled to −78° C. in a dry ice/acetone bath. Indene, 5.25 mL (45 mmole), is added to the solution which is then allowed to warm to room temperature. The solution is stirred at least 12 hours at room temperature prior to further reaction. Titration of the sample shows the reaction is complete.

Step (3) Reaction of lithium indenide with dichlorotitanium bis(dimethylamide).

A 500 mL Schlenk flask is charged with dichlorotitanium bis(dimethylamide), 7.24 g (35 mmole), and toluene, 100 mL. The mixture is stirred magnetically and chilled to −78° C. in a dry ice/acetone bath. Lithium indenide (4A-2), 45 mmole, is added to the mixture which is then allowed to warm slowly to room temperature. The mixture is stirred approximately 15 hours at room temperature. All volatiles are removed under vacuum at room temperature giving a dark viscous oil. The residue is extracted with toluene (1×50 mL) and filtered. The solution is chilled to −30° C. resulting in the formation of red/orange needles. The product is isolated by decanting the solution then vacuum drying the crystalline product. A proton NMR of the product shows it is pure indenyltitanium bis(dimethylamide) chloride. A test for chloride confirms the presence of the halide in the product.

Step (4) Preparation of lithium diethylamide.

A 100 mL Schlenk flask is charged with diethyl ether, 40 mL, then chilled to −78° C. n-Butyllithium, 0.73 mL of a 2.60M solution in hexane (1.92 mmole) is added to the magnetically stirred flask followed by the addition of diethylamine, 0.22 mL (2.11 mmole). The contents of the flask are maintained at or below −20° C. during this step. The mixture is warmed to room temperature and stirred at least 12 hours.

Step (5) Reaction of indenyltitanium bis(dimethylamide) chloride with lithium diethylamide.

A 250 mL Schlenk flask is charged with indenyltitanium bis(dimethylamide) chloride, 0.5 g (1.74 mmole), and diethyl ether, 50 mL. The magnetically stirred mixture is chilled to −20° C. while the solution of lithium diethylamide (4A-4) is added via canula. The solution is slowly warmed to room temperature and stirred at least 12 hours. The mixture is refluxed 1 hour. All volatiles are removed under vacuum at room temperature leaving an oily residue. The residue is extracted with hexane (1×50 mL) and filtered. Hexane is removed under vacuum leaving a red-brown oil which is placed under high vacuum (less than 1×10$^{-6}$ Torr) for an additional 8 hours to remove free indene and any other moderately high boiling volatiles. Chloride analysis indicated no residual chloride is present in the product. NMR indicated the product is sufficiently pure for use without further purification. Yields for this reaction are typically in excess of 95%.

B. Preparation of indenyltitanium bis(dimethylamide) di-n-propylamide, VII.

Indenyltitanium bis(dimethylamide)chloride prepared in Example 4A, steps 1-3 is used for this preparation as the starting material.

Step (1) Preparation of lithium di-n-propylamide.

A 100 mL Schlenk flask is charged with diethyl ether, 50 mL, and n-butyllithium, 1.4 mL of a 2.76M solution (3.84 mmole) in hexane, at −78° C. The magnetically stirred mixture is maintained at −78° C. in a dry ice/acetone bath during the next step. To the flask is added di-n-propylamine, 0.6 mL (4.22 mL), and the mixture is warmed to room temperature. The mixture is stirred approximately 7 hours at room temperature.

Step (2) Reaction of indenyltitanium bis(dimethylamide) chloride with lithium di-n-propylamide.

A 250 mL Schlenk flask is charged with indenyltitanium bis(dimethylamide) chloride, 1.00 g (3.49 mmole), and diethyl ether, 75 mL. The magnetically stirred mixture is maintained below −20° C. in an ice bath during addition of lithium di-n-propylamide prepared in 4B-1. The contents of the flask are stirred an additional 8 hours at room temperature then refluxed 2 hours. All volatiles are removed under vacuum leaving a darkly colored viscous residue. The residue is extracted with hexane (1×50 mL) then filtered. Hexane is removed under vacuum at room temperature leaving a red-brown oil which is placed under high vacuum (1×10$^{-6}$ Torr) to remove excess or free indene. Chloride analysis and NMR indicate the product is sufficiently pure indenyltitanium bis(dimethylamide) diethylamide, VII, and is used for polymerization runs without further purification.

C. Preparation of indenyltitanium bis(diethylamide) dimethylamide, VIII.

Step (1) Preparation of dichlorotitanium bis(diethylamide).

A 250 mL Schlenk flask is charged with toluene, 150 mL, and titanium tetrakis(diethylamide), 9.49 g (28.2 mmoles). To the magentically stirred mixture is added titanium tetrachloride, 5.35 g (28.2 mmole), resulting in the immediate formation of a brown solution. The mixture is stirred and refluxed 1 hour. All volatiles are removed under vacuum at room temperature leaving a brown oil. The oil is transferred to a short path microdistillation apparatus and the residue is distilled under vacuum. A red-brown oil is distilled from the residue at 95°–103° C. (0.05 mm Hg) which is determined to be $TiCl_2(NEt_2)_2$. The product yield is 78%.

Step (2) Preparation of lithium indenide.

A 100 mL Schlenk flask is charged with diethyl ether, 50 mL, and n-butyllithium, 5.5 mL of a 2.78M solution is hexane (16 mmoles), while stirring magnetically and maintaining the temperature at or below −20° C. in a dry ice/acetone bath. Nitrogen degassed indene, 2.0 mL (16.8 mmoles), is added to the chilled, stirred solution. The mixture is warmed to room temperature and stirred approximately 15 hours followed by refluxing for 1 hour. The reaction is assumed to be stoichiometric and complete based on titration data obtained from previous preparations of lithium indenide.

Step (3) Reaction of lithium indenide with dichlorotitanium bis(diethylamide).

A 250 mL Schlenk flask is charged with dichlorotitanium bis(diethylamide), 4 g (15.20 mmole), and diethylether, 50 mL. The magnetically stirred mixture is chilled to below −78° C. for the next step. Lithium indenide (16 mmoles), Example 4C step 2, is added to the 250 mL Schlenk flask via cannula and the mixture is allowed to slowly warm to room temperature. A reaction is apparent at −50° C. by the formation of an orange precipitate. The mixture is stirred approximately 15 hours at room temperature then refluxed one hour. All volatiles are removed under vacuum at room temperature leaving a deep orange powder. The residue is extracted with hexane (5×50 mL) and each extract is filtered then combined. The solvent volume of the extracts is reduced under vacuum and chilled to −30° C. Orange crystals are obtained which are vacuum dried. An NMR of the product revealed it is pure indenyltitanium bis(diethylamide) chloride. The yield is 4.2 g or 81%.

Step (4) Preparation of lithium diemthylamide.

A 100 mL Schlenk flask is charged with diethyl ether, 50 mL, then chilled to −78° C. To the magentically stirred solvent is added n-butyllithium, 1.8 mL of a 2.78M solution is hexane (5.04 mmole). Anhydrous dimethylamine, 0.4 mL (5.80 mmole) is added to the chilled solution via syringe. The mixture is warmed to room temperature then stirred 24 hours.

Step (5) Reaction of lithium dimethylamide with indenyltitanium bis(diethylamide) chloride.

The flask containing lithium dimethylamide prepared as described in Example 4C, step 4, is chilled to $-78°$ C. in a dry ice/acetone bath. A 100 mL Schlenk flask is charged with (Ind)TiCl(NEt$_2$)$_2$, 1.5 g (4.38 mmoles), and diethyl ether, 25 mL. The mixture is stirred magnetically in order to dissolve the complex. The solution containing (Ind)TiCl(NEt$_2$)$_2$ is added, via canula, to the magnetically stirred suspension containing lithium dimethylamide, Example 4C, step 4. The mixture immediately darkens and is warmed to room temperature. The reaction mixture is refluxed 1 hour then stirred an additional 12 hours at room temperature. All volatiles are removed under vacuum at room temperature leaving a deep brown oily residue. The residue is placed under high vacuum ($1 \times 10^{-6}$ Torr) at room temperature for several hours in order to remove any unreacted volatiles, such as indene. The residue is extracted with hexane ($1 \times 50$ mL) and all solvent is removed under vacuum leaving a deep red viscous liquid. The residue is again placed under high vacuum for several hours. An NMR of the residue showed the product to be primarily (Ind)Ti(NEt$_2$)$_2$(NMe$_2$), VIII. The yield is in excess of 95%.

D. Preparation of indenyltitanium bis(diethylamide) di-n-propylamide, IX.

Indenyltitanium bis(diethylamide) chloride prepared in Example 4C, steps 1-3 is used for this preparation as the starting material.

Step (1) Preparation of lithium di-n-propylamide.

A 100 mL Schlenk flask is charged with diethylether, 50 mL, and chilled to $-78°$ C. in a dry ice/actone bath. To the magnetically stirred flask is added n-butyllithium, 1.2 mL of a 2.78M solution in hexane (3.21 mmole), followed by di-n-propylamine, 0.5 mL (3.53 mmole). The contents are warmed to room temperature then stirred an additional 15 hours.

Step (2) Reaction of lithium di-n-propylamide with indenyltitanium bis(diethylamide) chloride.

A 250 mL Schlenk flask is charged with indenyltitanium bis(diethylamide) chloride, 1 g (2.92 mmole), and diethylether, 100 mL. The mixture is chilled to $-78°$ C. in a dry ice acetone bath and stirred magentically. The lithium di-n-propylamide prepared in Example 4D, step 1, is added to the flask via cannula. The mixture is slowly warmed to room temperature while stirring. The mixture is then refluxed approximately 2 hours. All volatiles are removed under vacuum at room temperature leaving a deeply colored yellow-brown, viscous oil. The residue is placed under high vacuum, $1 \times 10^{-6}$ Torr, for a few hours in order to remove any unreacted indene. Chloride analysis and NMR indicate the product is sufficiently pure indenyltitanium bis(diethylamide) di-n-propylamide, IX, and is used without further purification.

EXAMPLE 5

POLYMERIZATION

Following is the method employed for the polymerization reaction and is used in all examples in Table II. A stirred, one gallon (3.79 liter) batch reactor containing two liters of ISOPAR E and optionally a comonomer is heated to the desired polymerization temperature and the solvent vapor pressure recorded. To this an amount of hydrogen is optionally added which is recorded as the differential pressure drop from a 75 mL pressurized tank. The reactor is then pressurized with ethylene to give the final desired reactor pressure which is approximately 450 PSIG (3.10 MPa). An amount of catalyst is injected into the reactor determined by the total amount of product desired over time or until the catalyst is no longer active. For solution conditions the amount of catalyst injected or duration of the polymerization run is limited to avoid conditions in which the polymer precipitates from the solution phase. Ethylene reactor pressure is maintained at a constant level by a demand feed regulator to replace the ethylene consumed by the polymerization reaction. The total reaction time is held constant or varied based on desired yields of polymer. The results are given in Table II.

EXAMPLE 6

PREPARATION OF CATALYST COMPOSITIONS

An amount of catalyst is dissolved in ISOPAR ™ E to give a known concentration of the transition metal complex. An aliquot is injected into the reactor based on the formulated concentration to give the appropriate amount of transition metal complex expressed in $\mu$mole of Ti. The concentration of the complex in the inert diluent (ISOPAR ™ E) is completely arbitrary and not critical to catalyst preparation. The only consideration should be the volume of the injection pressure vessel which should accommodate the entire aliquot. Concentrations are adjusted to insure that the entire aliquot(s) of the catalyst component(s) are accommodated by the injection pressure vessel.

(1) A 0.001M solution of indenyltitanium bis(dimethylamide) diethylamide is prepared by dissolving 0.032 g (100 $\mu$mole) in Isopar ™ E, 100 mL. 20 mL of this solution is injected into the reactor.

(2) A 0.001M solution of indenyltitanium bis(dimethylamide) diethylamide is prepared by dissolving 0.032 g (100 $\mu$mole) in Isopar ™ E, 100 mL. 40 mL of this solution is injected into the reactor.

(3) A 0.001M solution of indenyltitanium bis(dimethylamide) di-n-propylamide is prepared by dissolving 0.035 g (100 $\mu$mole) in Isopar ™ E, 100 mL. 20 mL of this solution is injected into the reactor.

(4) A 0.002M solution of indenyltitanium bis(diethylamide) dimethylamide is prepared by dissolving 0.035 g (100 $\mu$mole) in Isopar ™ E, 50 mL. 20 mL of this solution is injected into the reactor.

(5) A 0.002M solution of indenyltitanium bis(diethylamide) di-n-propylamide is prepared by dissolving 0.041 g (100 $\mu$mole) in Isopar ™ E, 50 mL. 20 mL of this solution is injected into the reactor.

TABLE II

|  | Run Number | | | |
| --- | --- | --- | --- | --- |
|  | O | P | Q | R |
| Source of Complex, Ex. | 4-A | 4-A | 4-B | 4-C |
| Cat. Prep., Ex. | 6 (1) | 6 (2) | 6 (3) | 6 (4) |
| Comonomer, | | | | |
| Type | Octene | Octene | Octene | Octene |
| mL | 345 | 345 | 345 | 345 |
| Reactor Temp., °C. | 150 | 175 | 150 | 150 |
| $\Delta H_2$ | | | | |
| psig | 50 | 25 | 100 | 100 |
| kPa | 344.7 | 172.4 | 689.5 | 689.5 |
| Ti, $\mu$mole | 20 | 40 | 20 | 40 |
| Run Time, min. | 15.0 | 6.0 | 20.7 | 20.0 |
| Eff. kgPE/g-Ti | 95 | 11 | 156 | 21 |

TABLE II-continued

| Melt Index$^a$, | | | | |
|---|---|---|---|---|
| $I_2$ | 5.02 | 1.64 | 18.8 | 7.65 |
| $I_{10}$ | 38.9 | 12.1 | 157.6 | 62.8 |
| Mol. Wt. Dist., $I_{10}/I_2$ | 7.74 | 7.38 | 8.39 | 8.21 |
| Density$^b$ | .9233 | .9380 | .9493 | .9426 |

| | Run Number | | |
|---|---|---|---|
| | S | T | U |
| Source of Complex, Ex. | 4-D | 4-D | 4-D |
| Cat. Prep., Ex. | 6 (5) | 6 (5) | 6 (5) |
| Comonomer, | | | |
| Type | Octene | Octene | Octene |
| mL | 345 | 345 | 345 |
| Reactor Temp., °C. | 150 | 140 | 160 |
| $\Delta H_2$, | | | |
| psig | 100 | 100 | 100 |
| kPa | 689.5 | 689.5 | 689.5 |
| Ti, μmole | 40 | 40 | 40 |
| Run Time, min. | 18.0 | 17.0 | 9.6 |
| Eff. kgPE/g-Ti | 46 | 62 | 24 |
| Melt Index$^a$, | | | |
| $I_2$ | 57.9 | 5.93 | 63.3 |
| $I_{10}$ | ND$^c$ | 53.9 | ND |
| Mol. Wt. Dist., $I_{10}/I_2$ | ND | 9.10 | ND |
| Density$^b$ | .9314 | .9310 | ND |

$^a$Melt index is determined by ASTM D 1238-86, condition "E" for $I_2$ and condition "N" for $I_{10}$.
$^b$Density is determined by ASTM D 1248-84.
$^c$Not determined.

What is claimed is:

1. A process for preparing catalytic compounds represented by the formula $LTi(NR^1{}_2)_3$ wherein L is a pi-bonded ligand selected from the group consisting of indenyl, $C_1$-$C_4$ alkyl substituted indenyl, —$OSiR_3$ substituted indenyl, and each $R_1$ is the same and is a $C_1$-$C_4$ alkyl group which process comprises (1) reacting in a solvent or reaction medium selected from the class of aliphatic or aromatic hydrocarbons a compound represented by the formula $Ti(NR^1{}_2)_4$ wherein each $R_1$ is the same and is a $C_1$-$C_4$ alkyl group; with a compound represented by the formula $R'(Ind)$ wherein R' is hydrogen, a $C_1$-$C_4$ alkyl group, —$OSiR_3$, —OR or a halogen; R is a $C_1$-$C_4$ alkyl group; and IND is an indenyl group; and (2) recovering the desired product from the reaction mixture.

2. A process of claim 1 wherein the reaction is conducted at a temperature from about −78° C. to the reflux temperature.

3. A process of claim 1 wherein the temperature is from about 0° C. to the reflux temperature.

4. A process of claim 1 wherein the components are combined at room temperature and then heated to the reflux temperature and L is indenyl and each R is independently methyl, ethyl or n-propyl.

5. A process of claim 1 wherein the aliphatic or aromatic solvent is selected from the group consisting of toluene, benzene, hexane, heptane, octane, isooctane, nonane, decane, kerosene, or any combination thereof.

* * * * *